United States Patent [19]

Dahl et al.

[11] 4,224,320
[45] Sep. 23, 1980

[54] NOVEL STEROIDS OF THE PREGNANE SERIES, SUBSTITUTED IN THE 17-POSITION, THEIR MANUFACTURE AND THEIR USE

[75] Inventors: Helmut Dahl; Ernst Schöttle; Reinhold Wieske; Alfred Weber; Mario Kennecke, all of Berlin, Fed. Rep. of Germany

[73] Assignee: Schering, Aktiengesellschaft, Berlin and Bergkamen, Fed. Rep. of Germany

[21] Appl. No.: 6,692

[22] Filed: Jan. 25, 1979

[30] Foreign Application Priority Data

Jan. 25, 1978 [DE] Fed. Rep. of Germany ....... 2803660

[51] Int. Cl.² .......................... A61K 31/56; C07J 9/00
[52] U.S. Cl. .................. 424/243; 260/397.4; 260/397.47
[58] Field of Search ............ 260/239.55, 397.4, 397.47

[56] References Cited

U.S. PATENT DOCUMENTS

| | | | |
|---|---|---|---|
| 3,187,025 | 6/1965 | Julian et al. | 260/397.47 |
| 3,510,556 | 5/1970 | Erb et al. | 260/239.55 |
| 3,530,117 | 9/1970 | Rosegay et al. | 260/239.5 |

*Primary Examiner*—Elbert L. Roberts
*Attorney, Agent, or Firm*—Millen & White

[57] ABSTRACT

Steroids of the formula

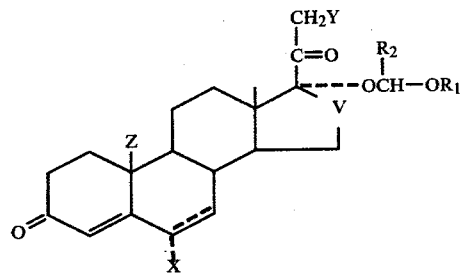

wherein
--- represents a single or double bond,
X is hydrogen, fluorine or methyl;
Y is hydrogen, hydroxy or alkanoyloxy of 1-6 carbon atoms;
Z is hydrogen or methyl;
V is methylene, ethylidene, hydroxymethylene or vinylidene; and
$R_1$ is alkyl of 1-6 carbon atoms or alkyl of 2-6 carbon atoms with an oxygen atom between two of the carbon atoms;
$R_2$ is hydrogen or alkyl of 1-6 carbon atoms, or
$R_1$ and $R_2$ together form a tri- or tetramethylene group provided that Y is hydroxy or alkanoyloxy;

have pharmacological activity and are useful as intermediates for preparing other pharmacologically active steroids.

27 Claims, No Drawings

NOVEL STEROIDS OF THE PREGNANE SERIES, SUBSTITUTED IN THE 17-POSITION, THEIR MANUFACTURE AND THEIR USE

CROSS REFERENCE TO RELATED APPLICATIONS

U.S. application Ser. No. 6,693, filed on Jan. 25, 1979, the same day as this application, and whose disclosure is incorporated by reference herein, concerns related compounds and processes.

BACKGROUND OF THE INVENTION

The present invention concerns new 17-substituted steroids, a process for making them and methods of using them.

As is known, 11 β-hydroxy steroids having anti-inflammatory activity (such as, for example, the corticoids: hydrocortisone, prednisolone, dexamethasone, betamethasone, prednylidene, triamcinolone, fluocinolone or flurandrenolone) are prepared by means of very expensive, multistage partial syntheses from naturally occurring steroids (such as diosgenin), whose procurement in adequate amounts is encountering increasing difficulties. Within the multistage syntheses of these compounds, the microbiological introduction of the 11 β-hydroxy group into the steroid skeleton normally is the most costly and most wasteful step of the synthesis.

A process was developed in 1966, by which the yield of 11β-hydroxylation of 11-deoxy-17α-hydroxy steroids of the pregnane series could be substantially increased. This process involves esterifying the 17 α-hydroxy group, then conducting a hydroxylation with the aid of fungi of the genus Curvularia, and saponifying the thus-obtained 11 β-hydroxy-17α-acyloxy steroids (German Pat. No. 1,618,599 = U.S. Pat. No. 3,530,038).

However, the acylation of the 17-hydroxy group is rather expensive; and the yields obtained thereby are frequently unsatisfactory.

The hydrolysis of the 11β-hydroxy-17 α-acyloxy steroids is likewise difficult since by-products are frequently formed. This requires an expensive and wasteful purification of the thus-obtained products so that the latter will satisfy the purity criteria demanded of active medicinal agents.

SUMMARY OF THE INVENTION

Accordingly, it is an object of the invention to provide a new process for preparing medicinally active steroids.

It is another object of the invention to provide new compounds which can be used as starting materials for preparing medicinally active steroids and a method for preparing the new compounds.

It is still another object of the invention to provide such compounds which are also themselves medicinally active.

Upon further study of the specification and appended claims, further objects and advantages of this invention will become apparent to those skilled in the art.

These objects have been achieved by providing compounds of formula I

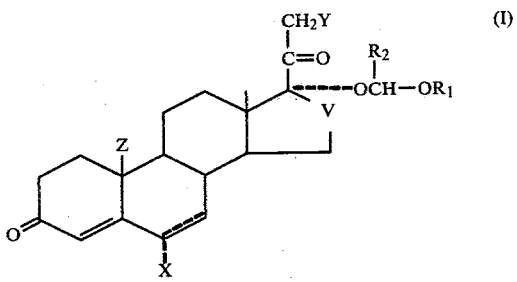

wherein
$\equiv\equiv\equiv$ represents a single or double bond,
X is hydrogen, fluorine or methyl;
Y is hydrogen, hydroxy or alkanoyloxy of 1–6 carbon atoms;
Z is hydrogen or methyl;
V is methylene, ethylidene, hydroxymethylene or vinylidene; and
$R_1$ is alkyl of 1–6 carbon atoms or alkyl of 2–6 carbon atoms with an oxygen atom between two of the carbon atoms,
$R_2$ is hydrogen or alkyl of 1–6 carbon atoms, or
$R_1$ and $R_2$ together form a tri- or tetramethylene group provided that Y is hydroxy or alkanoyloxy.

It has now been found that the process of the 11β-hydroxylation of steroids can be substantially improved by using as starting compound steroids for the microbiological reaction, instead of 11-deoxy-17-acyloxy steroids, steroids of formula I.

DETAILED DISCUSSION

Suitable alkyl groups, e.g. for $R_1$ and $R_2$, as well as for the alkyl portion of the alkanoyloxy groups, e.g., for Y, include, for example, alkyl groups of 1–6 carbon atoms, preferably straight chain ones, especially alkyl of 1–4 carbon atoms. Suitable such alkyl groups include, for example, propyl, butyl, isopropyl, sec-butyl and, particularly, methyl and ethyl. Suitable $C_{2-6}$ alkyl groups interrupted by an oxygen atom for $R_1$ and $R_2$ include preferably groups of 3–6 carbon atoms. Such groups include for example, 2-alkoxyethylene groups, such as 2-methoxyethylene and 2-ethoxyethylene.

The steroids of formula I can be produced in a simple way according to the process of this invention by reacting a steroid of the formula

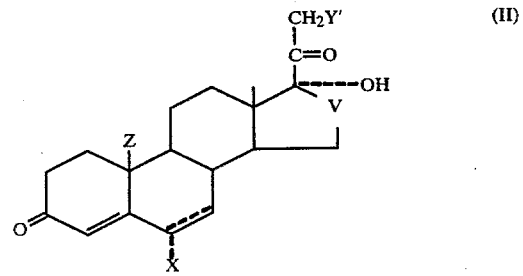

or of the formula

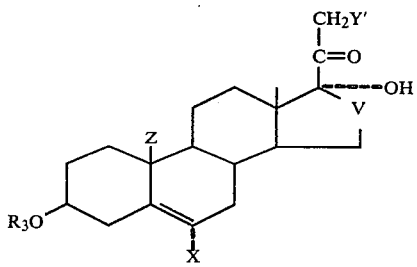

wherein

⚌, X, V and Z are defined above;

Y' is hydrogen or alkanoyloxy of 1–6 carbon atoms, and $R_3$ is alkanoyl of 1–6 carbon atoms, with an acetal of the formula $$R_2CH(OR_1)_2 \quad (IV)$$

or with a vinyl ether of the formula $$R_4CH{=}CH{-}OR_1 \quad (V)$$

wherein $R_1$ and $R_2$ are as defined for formula I and $R_4$ is hydrogen or alkyl of 1–5 carbon atoms, or $R_4$ together with $R_1$ is trimethylene or ethylene when Y, in the steroid of formula I to be prepared, is hydroxy or alkanoyloxy; and further optionally saponifying an ester group which is present or oxidizing a 3β-hydroxy group with simultaneous isomerization of the $\beta^5$-double bond.

The acetalization can be conducted under conditions known per se (Synthesis 1975: 2786; J. Chem. Soc. (c) 1974: 431; and J. Amer. Chem. Soc. 74: 1239 [1952]).

Thus it is possible, for example, to react a steroid of formula II or III with an acetal of formula IV in the presence of an acidic catalyst, e.g., perchloric acid, p-toluenesulfonic acid or, suitably, phosphorus pentoxide. This reaction can be conducted in the absence of further solvents or in the presence of inert solvents such as chloroform, methylene chloride, tetrachloroethane, tetrachloromethane, toluene, diethyl ether, tetrahydrofuran, dioxane, etc. The reaction is usually conducted at a temperature of −20° C. to +50° C., and is suitable, in particular, for the production of those steroids of formula I wherein $R_2$ is hydrogen.

On the other hand, the steroids of formula II or III can also be reacted with a vinyl ether of formula V. This reaction is preferably conducted in one of the aforementioned inert solvents with the addition of an acidic catalyst (perchloric acid, p-toluenesulfonic acid, methanesulfonic acid, etc.). The reaction is preferably effected at a reaction temperature of −20° C. to 100° C.

To obtain optimum yields, it is advantageous to vary the reaction parameters in preliminary experiments as is conventional to those skilled in the art.

It could not be foreseen by a person skilled in the art that the tertiary and additionally sterically hindered 17α-hydroxy group of the steroids of formula II and III could be acetalized or reacted with a vinyl ether in a practically quantitative fashion.

The optionally following saponification reaction can be effected under fully conventional conditions by reacting the previously obtained products in an aqueous or alcoholic solution with alkaline catalysts (potassium bicarbonate, sodium carbonate, potassium carbonate, sodium hydroxide, sodium methylate, etc.).

The optionally following oxidation of the 3 β-hydroxy group with simultaneous isomerization of the $\Delta^5$-double bond can be conducted, for example, under the conditions well known for the conventional "Oppenauer oxidation." (J. Fried and J. A. Edwards Organic Reactions in Steroid Chemistry; van Nostrand Reinhold Comp. New York, Vol 1, 1972, page 234 and 235).

The optionally following saponification, oxidation and isomerization can be accomplished with especially great success by reacting the compounds prepared from the starting steroids of Formula III with a culture of the species *Flavobacterium dehydrogenans* under conventional conditions for such reactions (U.S. Pat. Nos. 3,074,977 and 3,009,936).

The thus-obtained products of the process, i.e. the steroids of formula I, can then be hydroxylated in the 11 β-position under conditions conventional for the preparation of 11 β-hydroxy-17 α-acyloxy steroids (German Pat. No. 1,618,599, whose disclosure is incorporated by reference herein) in order to prepare steroids of the formula VI'

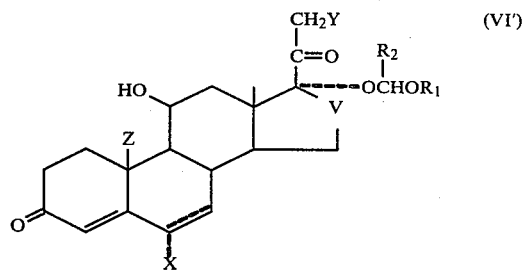

wherein ⚌, X, Z, V, Y, $R_1$ and $R_2$ are as defined for formula I.

After hydroxylation, the acetal group in the 17-position of the compounds of formula VI' can be split practically quantitatively to prepare compounds of the formula VI

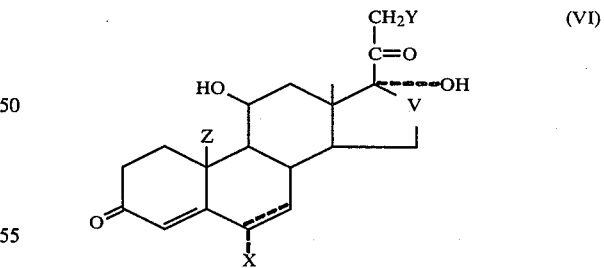

wherein ⚌, X, Y, Z and V are as defined for formula I.

This splitting step can be conducted under conditions conventionally employed for the hydrolysis or alcoholysis of acetals or ketales (C. Djerassi Steroid Reaktions, 1963, 2–83). The compounds can be cleaved, for example, by reaction with a mineral acid, such as hydrochloric acid, sulfuric acid, phosphoric acid or perchloric acid; a sulfonic acid, such as p-toluenesulfonic acid; a strongly acidic carboxylic acid, such as formic acid, acetic acid or trifluoroacetic acid; an acidic ion exchanger; or with a Lewis acid, such as boron trifluoride, zinc chloride, zinc bromide or titanium tetrachloride; in a lower alcohol, such as methanol or ethanol, or in an aqueous organic solvent, such as glycol monomethyl ether, tetrahydrofuran, dioxane, dimethylformamide, dimethyl sulfoxide, hexamethylphosphoric triamide or acetone. The reaction temperature normally is $-20°-+120°$ C.

The steroids of formulae VI are well known pharmacologically active corticoides, e.g., as anti-inflammatory agents.

The steroids of formula VI' which are disclosed in U.S. application Ser. No. 66,393 filed Jan. 25, 1979 are also pharmacologically active corticoides, e.g., anti-inflammatory agents.

The novel compounds of formula I, however, are not only valuable intermediates but also possess, moreover, good pharmacological efficacy, per se. They possess, for example, progestational and antiandrogenic an ovulation inhibiting activities.

Frequently, their activity surpasses that of the 17-hydroxy compounds, e.g., of formula II and/or the esters thereof. They are often also distinguished by a favorable dissociation between the desired effectiveness and their undesired side effects.

Thus, the compounds of formula I can be employed as medicaments and can be processed in accordance with conventional methods of galenic pharmacy to produce medicinal agents. Conventional excipients are pharmaceutically acceptable organic or inorganic carrier substances suitable for parenteral, or enteral application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg. in a pharmaceutically acceptable carrier per unit dosage.

The dosage of the compounds according to this invention is 10–500 mg/day when administered to human patients as a capsule, pill, tablete or dragee in the same manner as the known.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(a) 21.63 g. of $3\beta,21$-diacetoxy-$17\alpha$-hydroxy-5-pregnen-20-one is dissolved in 150 ml. of anhydrous methylene chloride and 100 ml. of anhydrous formaldehyde dimethylacetal. The solution is then cooled with water and introduced into a mixture of 21.6 g. of phosphorus pentoxide and 43 g. of kieselguhr, and the mixture is stirred for one hour at room temperature. The reaction mixture is then filtered, the residue is washed with methylene chloride, triethylamine is added to the filtrate until a pH of 9 has been reached, and the mixture is concentrated under vacuum. The residue is recrystallized from methanol/methylene chloride, thus obtaining 22.68 g. of $\beta,21$-diacetoxy-$17\alpha$-methoxymethoxy-5-pregnen-20-one, m.p. 182°–184° C.

(b) A 2-liter Erlenmeyer flask containing 1 liter of sterile nutrient solution which contains 0.3% yeast extract, 0.3% corn steep liquor, and 0.2% glucose—adjusted to pH 7.0 —is inoculated with a dry culture of *Flavobacterium dehydrogenas* ATCC 13 930 and shaken at 30° C. for two days at 175 r.p.m.

A 500-milliliter Erlenmeyer flask with 85 ml. of the same nutrient medium is inoculated with 10 ml. of the Flavobacterium dehydrogenas germination culture and shaken at 175 r.p.m. at 30° C. for 7 hours. Then 5 ml. of a sterile solution of 0.5 g. of $3\beta,21$-diacetoxy-$17$-$\alpha$-methoxymethoxy-5-pregnen-20-one in dimethylformamide is added to the culture, and the latter is shaken at 30° C. for another 65 hours at 175 r.p.m. After fermentation has been completed, the culture is extracted twice with 100 ml. of ethylene chloride. The extract is concentrated under vacuum, the residue is purified by chromatography over aluminum oxide, and the yield is 402 mg. of 21-hydroxy-$17\alpha$-methoxymethoxy-4-pregnene-3,20-dione, m.p. 152–153° C.

(c) A 2-liter Erlenmeyer flask with 1 liter of a sterile nutrient solution containing 2% glucose and 2% corn steep liquor—adjusted to pH 6.5 —is inoculated with a supernatent broth of a dry culture of *Curvularia lunata* NRRL 2380 and shaken at 175 r.p.m. for 60 hours at 30° C.

A 500-milliliter Erlenmeyer flask with 90 ml. of a sterile nutrient medium containing 1.0% corn steep liquor and 1.25% soybean powder—adjusted to pH 6.2 —is inoculated with 10 ml. of the Curvularia lunata germination culture and shaken at 3020 C. for 7 hours at 175 r.p.m. Then 0.6 ml. of a sterile solution of 30 mg. of 21-hydroxy-$17\alpha$-methoxymethoxy-4-pregnene-3,20-dione in dimethylformamide is added to the culture, and the latter is further fermented for 65 hours under the above-described conditions.

The fermentation culture is worked up as set forth in Example 1(b), thus obtaining 27 mg. of $11\beta$, 21-dihydroxy-$17\alpha$-methoxymethoxy-4-pregnene-3,20-dione, m.p. 180°–182° C.

(d) 2.5 g. of $11\beta,21$-dihydroxy-$17\alpha$-methoxymethoxy-4-pregnene-3,20-dione is dissolved in 40 ml. of anhydrous methylene chloride, cooled to 0° C., and combined within 15 minutes under argon with a solution of 2.25 ml. of titanium tetrachloride in 10 ml. of methylene chloride. The reaction mixture is thereafter stirred at room temperature for 90 minutes. Then, 150 ml. of methylene chloride and 100 ml. of saturated aqueous sodium bicarbonate solution are added thereto; the mixture is stirred for 15 minutes, the organic phase is separated, washed neutral, dried over sodium sulfate, and concentrated under vacuum. The residue is recrystallized from chloroform, thus obtaining 2.19 g. of 11β,17α,21-trihydroxy-4-pregnene-3,20-dione, decomposition point: 215° C.

EXAMPLE 2

(a) 50 g. of 3β,21-diacetoxy-17α-hydroxy-5-pregnen-20-one is combined with 50 mg. of anhydrous p-toluenesulfonic acid and 350 ml. of anhydrous methylene chloride, cooled to 0° C., and, after adding 10 g. of methylvinyl ether, stirred at 0° C. for 4 hours. Then triethylamine is added to the reaction mixture until a pH of 9 has been reached, and the mixture is concentrated under vacuum. Yield: 58 g. of 3β,21-diacetoxy-17α(1'-methoxyethoxy)-5-pregnen-20-one as a diastereomeric mixture, m.p. 80°–118° C. (A sample recrystallized from methanol melts at 132°–134° C.)

(b) Under the conditions of Example 1(b), a solution of 600 mg. of 3β,21-diacetoxy-17α-(1'-methoxyethoxy)-5-pregnen-20-one, mixture of diastereomers, in 5 ml. of dimethylformamide is reacted with a *Flavobacterium dehydrogenas* ATCC 13 930 culture and worked up, thus obtaining 394 mg. of 21-hydroxy-17α-(1'-methoxyethoxy)-4-pregnene-3,20-dione as a diastereomeric mixture, m.p. 166°–178° C.

(c) A solution of 100 mg. of 21-hydroxy-17α-(1'-methoxyethoxy)-4-pregnene-3,20-dione, diastereomeric mixture, in 2 ml. of dimethylformamide is fermented with a culture of *Culvularia lunata* NRRL 2380 under the conditions described in Example 1(c), then worked up, and the product is 105 mg. of 11β,21-dihydroxy-17α-(1'methoxyethoxy)-4-pregnene-3,20-dione as an oily mixture of diastereomers.

This mixture is combined with 3 ml. of methanol and 0.5 ml. of 2N aqueous hydrochloric acid and shaken for 5 hours at room temperature. Subsequently 4 ml. of water is added to the mixture, and the latter is neutralized with saturated aqueous sodium bicarbonate solution, extracted twice with respectively 8 ml. of ethylene chloride, the organic phase concentrated under vacuum, the residue purified by chromatography over an aluminum oxide column, and the yield is 69 mg. of 11β,17α,21-trihydroxy-4-pregnene-3,20-dione, m.p. 217°–219° C.

EXAMPLE 3

(a) 10.0 g. of 21-acetoxy-17α-hydroxy-4-pregnene-3,20-dione is combined with 13 mg. of anhydrous p-toluenesulfonic acid and 130 ml. of anhydrous methylene chloride, cooled to 0° C., and stirred, after adding 2.3 g. of methylvinyl ether, for 7 hours at 0° C. The reaction mixture is worked up as set forth in Example 2(a), thus obtaining 11.6 g. of 21-acetoxy-17α-(1'-methoxyethoxy)-4-pregnene-3,20-dione, m.p. 135°–150° C.

(b) A solution of 0.1 g. of 21-acetoxy-17α-(1'-methoxyethoxy)-4-pregnene-3,20-dione, diastereomeric mixture, in 2 ml. of dimethylformamide is fermented with a culture of *Curvularia lunata* NRRL 2380 under the conditions described in Example 1(c), and then worked up. The thus-obtained 11β,21-dihydroxy-17α-(1'-methoxyethoxy)-4-pregnene-3,20-dione is then hydrolyzed under the conditions described in Example 2(c), thus obtaining 78 mg. of 11β,17α,21-trihydroxy-4-pregnene-3,20-dione, m.p. 217°–219° C.

EXAMPLE 4

(a) 10.0 g. of 21-acetoxy-17α-hydroxy-4-pregnene-3,20-dione is reacted, under the conditions described in Example 3(a), with 2.50 g. of ethylvinyl ether, worked up, and the product is 12.5 g. of 21-acetoxy-17α-(1'-ethoxyethoxy)-4-pregnene-3,20-dione in the form of an oily mixture of diastereomers.

(b) A solution of 0.1 g. of 21-acetoxy-17α-(1'-ethoxyethoxy)-4-pregnene-3,20-dione, diastereomeric mixture, in 2 ml. of dimethylformamide is hydroxylated with *Curvularia lunata* NRRL 2380 under the conditions described in Example 1(c), then worked up, and the product is 17α-(1'-ethoxyethoxy)-11β,21-dihydroxy-4pregnene-3,20-dione; the latter is hydrolyzed under the conditions described in Example 2(c) to 63 mg. of 11β,17α,21-trihydroxy-4-pregnene-3,20-dione, m.p. 216°–217.5° C.

EXAMPLE 5

(a) 10.0 g. of 21-acetoxy-17α-hydroxy-4-pregnene-3,20-dione is reacted with 4.0 g. of isobutylvinyl ether under the conditions described in Example 3(a) and then worked up, thus obtaining 13.5 g. of 21-acetoxy-17α-(1'-isobutoxyethoxy)-4-pregnene-3,20-dione as an oily mixture of diastereomers.

(b) A solution of 0.1 g. of 21-acetoxy-17α-(1'-isobutoxyethoxy)-4-pregnene-3,20-dione, mixture of diastereomers, in 2 ml. of dimethylformamide is hydroxylated with *Curvularia lunata* NRRL 2380 under the conditions set forth in Example 1(c) and then worked up, thus producing 11β,21-dihydroxy-17α-(1'-isobutoxyethoxy)-4-pregnene-3,20-dione; the latter is saponified under the conditions indicated in Example 2(c) to 68 mg. of 11β, 17α,21-trihydroxy-4-pregnene-3,20-dione, m.p. 214°–216° C. (decomposition).

EXAMPLE 6

(a) 1.95 g. of 21-acetoxy-17α-hydroxy-4-pregnene-3,20-dione is combined with 5 mg. of anhydrous p-toluenesulfonic acid, 25 ml. of anhydrous methylene chloride, and 3.5 ml. of dihydropyran and stirred for 13 hours at room temperature. The reaction mixture is worked up as set forth in Example 3(a), thus obtaining 2.0 g. of 21-acetoxy-17α-(2'-tetrahydropyranyloxy)-4-pregnene-3,20-dione as a diastereomeric mixture, m.p. 185°–200° C.

(b) A solution of 0.1 g. of 21-acetoxy-17α-(2'-tetrahydropyanyloxy)-4-pregnene-3,20-dione, diastereomeric mixture, in 2 ml. of dimethylformamide is hydroxylated with *Curvularia lunata* NRRL 2380 under the conditions described in Example 1(c) and worked up, thus obtaining 11β,21-dihydroxy-17α-(2'-tetrahydropyranyloxy)-4-pregnene-3,20-dione; the latter is hydrolyzed under the conditions set forth in Example 2(c) to 72 mg. of 11β,17α,21-trihydroxy-4-pregnene-3,20-dione, m.p. 215° C. (decomposition).

EXAMPLE 7

(a) 50 g. of 21-acetoxy-17α-hydroxy-6α-methyl-4-pregnene-3,20-dione is reacted with 13.9 g. of methylvinyl ether under the conditions described in Example 3(a) and worked up, thus producing 59 g. of 21-acetoxy-17α-('-methoxyethoxy)-6α-methyl-4-pregnene-3,20-dione as an amorphous mass.

(b) A solution of 200 mg. of 21-acetoxy-17α-(1'-methoxyethoxy)-6α-methyl-4-pregnene-3,20-dione in 0.4 ml. of dimethylformamide is hydroxylated under the conditions described in Example 1(c) with *Curvularia lunata* NRRL 2380 and worked up, yielding 11β,21-dihydroxy-17α-(1'-methoxyethoxy)-6α-methyl-4-pregnene-3,20-dione which is hydrolyzed under the conditions set forth in Example 2(c) to 15 mg. of 11β,17α,21-trihydroxy-6α-methyl-4-pregnene-3,20-dione, m.p. 189°–192° C.

EXAMPLE 8

(a) 2.0 g. of 21-acetoxy-17α-hydroxy-16β-methyl-4-pregnene-3,20-dione is combined with 5 mg. of p-toluenesulfonic acid (anhydrous) and 25 ml. of anhydrous methylene chloride and cooled to 0° C. The 0.5 g. of methylvinyl ether is added to the mixture under agitation, and the mixture is stirred for 5 hours at 0° C. and for another 12 hours at room temperature and then worked up as described in Example 3(a). Yield: 2.1 g. of 21-acetoxy-17α-(1'-methoxyethoxy)-16β-methyl-4-pregnene-3,20-dione as an oily mixture of diastereomers.

(b) A solution of 50 mg. of 21-acetoxy-17α-(1'-methoxyethoxy)-16β-methyl-4-pregnene-3,20-dione, diastereomeric mixture, in 1 ml. of dimethylformamide is hydroxylated with *Curvularia lunata* NRRL 2380 under the conditions indicated in Example 1(c), thus obtaining 11β,21-dihydroxy-17α-(1'-methoxyethoxy)-16β-methyl-4-pregnene-3,20-dione which is hydrolyzed under the conditions described in Example 2(c) to 32 mg. of 11β,17α,21-trihydroxy-16β-methyl-4-pregnene-3,20-dione, m.p. 204°–207° C.

EXAMPLE 9

(a) 50 g. of 17α-hydroxy-4-pregnene-3,20-dione is reacted with 15 g. of methylvinyl ether under the conditions set forth in Example 3(a) and worked up, thus producing 51.2 g. of 17α-(1'-methoxyethoxy)-4-pregnene-3,20-dione, m.p. 115°–152° C.

(b) A solution of 0.1 g. of 17α-(1'-methoxyethoxy)-4-pregnene-3,20-dione in 1 ml. of dimethylformamide is fermented under the conditions described in Example 1(c) with a culture of *Curvularia lunata* NRRL 2380 and worked up. The thus-obtained 11β-hydroxy-17α-(1'-methoxyethoxy)-4-pregnene-3,20-dione (m.p. 85°–103° C.) is hydrolyzed under the conditions indicated in Example 2(c), thus obtaining 63 mg. of 11β,17α-dihydroxy-4-pregnene-3,20-dione, m.p. 222°–223.5° C.

EXAMPLE 10

(a) 50 g. of 3β,21-diacetoxy-17α-hydroxy-5-pregnen-20-one is reacted under the conditions described in Example 1(a) in 150 mg. of methylene chloride with 380 g. of formaldehyde bis-glycol monomethyl ether acetal, 50 g. of phosphorus pentoxide, and 100 g. of kieselguhr and worked up, thus obtaining 45.8 g. of 3β,21-diacetoxy-17α-(2'-methoxyethoxymethoxy)-5-pregnen-20-one, m.p. 160°–161° C.

(b) Under the conditions described in Example 1(b), 0.5 g. of 3β,21-diacetoxy-17α-(2'-methoxyethoxymethoxy)-5-pregnen-20-one is reacted with a culture of *Flavobacterium dehydrogenas* ATCC 13 930 and worked up. Yield: 390 mg. of 21-hydroxy-17α-(2'-methoxyethoxymethoxy)-4-pregnene,3,20-dione as a vitreous mass.

(c) Under the conditions of Example 1(c), 30 mg. of 21-hydroxy-17α-(2'-methoxyethoxymethoxy)-4-pregnene-3,20-dione is reacted with a culture of *Curvularia lunata* NRRL 2380 and worked up, thus producing 24 mg. of 11β,21-dihydroxy-17α-(2'-methoxyethoxymethoxy)-4-pregnene-3,20-dione, m.p. 143°–147° C.

(d) Under the conditions of Example 1(d), 10 mg. of 11β,21-dihydroxy-17α-(2'-methoxyethoxymethoxy)-4-pregnene-3,20-dione is reacted in 2 ml. of methylene chloride and 0.01 ml. of titanium tetrachloride and worked up, thus obtaining 8 mg. of 11β,17α,21-trihydroxy-4-pregnene-3,20-dione, decomposition point 213° C.

EXAMPLE 11

20 g. of 3β-acetoxy-17α-hydroxy-5-pregnen-20-one is reacted under the conditions mentioned in Examples 1(a) through 1(c), thus obtaining 15 g. of 17α-methoxymethoxy-4-pregnene-3,20-dione.

EXAMPLE 12

3 g. of 17α-hydroxy-19-nor-4-pregnene-3,20-dione is suspended in 75 ml. of formaldehyde dimethylacetal, cooled in an ice bath, and combined in incremental portions with a mixture of 7.5 g. of kieselguhr and 4.5 g. of phosphorus pentoxide. After three hours, the mixture is filtered and the filtrate is brought to pH 9 with triethylamine. After the solvents have been distilled off under vacuum, an oil is obtained which is chromatographed on silica gel with toluene/ethyl acetate mixtures, thus obtaining 1.48 g. of 17α-methoxymethoxy-19-nor-4-pregnene-3,20-dione, melting at 120° C. after recrystallization from methanol.

EXAMPLE 13

5 g. of 17α-hydroxy-19-nor-4-pregnene-3,20-dione is dissolved in 140 ml. of methylene chloride and reacted with 30 ml. of formaldehyde diethylacetal, 10 g. of kieselguhr, and 5 g. of phosphorus pentoxide at ice bath temperature as described hereinabove. Yield: 2.98 g. of 17α-ethoxymethoxy-19-nor-4-pregnene-3,20-dione, melting at 69°–71° C. after crystallization with pentane.

EXAMPLE 14

5 g. of 17α-hydroxy-19-nor-4-pregnene-3,20-dione is dissolved in 140 ml. of methylene chloride and reacted as described above with 40 ml. of formaldehyde dipropylacetal, 10 g. of kieselguhr, and 5 g. of phosphorus pentoxide, thus obtaining 3.13 g. of 17α-propoxymethoxy-19-nor-4-pregnene-3,20-dione which melts, after crystallization with pentane, at 97°–99° C.

EXAMPLE 15

50 g. of 21-acetoxy-17α-hydroxy-4-pregnene-3,20-dione is suspended with 600 ml. of formaldehyde diethylacetal and 600 ml. of methylene chloride and cooled to −30° to −40° C. Under agitation, a mixture of 75 g. of phosphorus pentoxide and 150 g. of kieselguhr is introduced, and the mixture is stirred for 30 hours at −30° C. The solution is filtered and neutralized with triethylamine. After the solvents have been distilled off, the mixture is once more distilled off with methanol, and the residue is recrystallized from methanol, thus obtaining 35.9 g. of 21-acetoxy-17α-ethoxymethoxy-4-pregnene-3,20-dione which melts at 137°–139° C. after another recrystallization.

EXAMPLE 16

25 g. of 21-acetoxy-17α-hydroxy-4-pregnene-3,20-dione is suspended with 200 ml. of formaldehyde dipropylacetal and 320 ml. of methylene chloride and cooled to −20° C. Under agitation, a mixture of 49.3 g.

of phosphorus pentoxide and 97 g. of kieselguhr is introduced, and the mixture is stirred for 22 hours at −20° C. The solution is filtered and neutralized with triethylamine. The methylene chloride is distilled off under vacuum, and the formaldehyde dipropylacetal phase is decanted from the separated oil. After additional solvent has been distilled off under vacuum, 19 g. of 21-acetoxy-17α-propoxymethoxy-4-pregnene-3,20-dione is crystallized, m.p. 145°–147° C.

EXAMPLE 17

50 g. of 21-acetoxy-17α-hydroxy-4-pregnene-3,20-dione is suspended with 500 ml. of formaldehyde dibutylacetal and 500 ml. of methylene chloride and cooled to −35° C. Under agitation, a mixture of 74 g. of phosphorus pentoxide and 150 g. of kieselguhr is introduced, and the mixture is stirred for 30 hours at −35° C. The solution is filtered and neutralized with triethylamine. The methylene chloride is destilled off under vacuum and the formaldehyde dibutylacetal phase is decanted from the separated oil. After additional solvent has been distilled off under vacuum, 38.7 g. of 21-acetoxy-17α-butoxymethoxy-4-pregnene-3,20-dione is crystallized, m.p. 123.5°–124.5° C.

EXAMPLE 18

10.60 g. of 21-acetoxy-6α-fluoro-17α-hydroxy-4-pregnene-3,20-dione is dissolved in 265 ml. of methylene chloride and 47.7 ml. of formaldehyde dimethylacetal. A mixture of 7.95 g. of phosphorus pentoxide and 15.9 g. of kieselguhr is added in incremental portions, and the mixture is stirred for 90 minutes under nitrogen at room temperature. The solution is filtered and combined with 2.1 ml. of triethylamine. The solvents are distilled off and the residue recrystallized from methanol, thus obtaining 7.6 g. of 21-acetoxy-6α-fluoro-17α-methoxymethoxy-4-pregnene-3,20-dione, m.p. 161°–167° C.

EXAMPLE 19

43 g. of 3β,21-diacetoxy-17α-hydroxy-16β-methyl-5-pregnen-20-one is dissolved in 800 ml. of formaldehyde dimethylacetal and cooled to −15° C. In incremental portions, a mixture of 43 g. of phosphorus pentoxide and 86 g. of kieselguhr is added; the mixture is stirred for 15 hours at about −15° C. The solution is filtered, neutralized with triethylamine, and the solvents are distilled off under vacuum. The residue is recrystallized with methanol, thus obtaining 31.5 g. of 3β,21-diacetoxy-17α-methoxymethoxy-16β-methyl-5-pregnen-20-one, m.p. 117°–118° C. *Flavobacterium dehydrogenans* ATCC 13 930 is germinated as described in Example 1 (b) and fermented. At the 7th hour 4 ml. of a sterile solution of 0.2 g. of 3β,21-diacetoxy-17α-methoxymethoxy-16β-methyl-5-pregnen-20-one in dimethylformamide is added to the culture, and the latter is shaken for another 65 hours.

After fermentation has been completed, the culture is worked up as set forth in Example 1 (b), thus obtaining 163 mg. of 21-hydroxy-17α-methoxymethoxy-16β-methyl-4-pregnene-3,20-dione, m.p. 126°/128°–129° C.

EXAMPLE 20

29.1 g. of 21-acetoxy-6-chloro-17α-hydroxy-4,6-pregnadiene-3,20-dione is dissolved in 730 ml. of methylene chloride and 131.0 ml. of formaldehyde dimethylacetal. A mixture of 22.12 g. of phosphorus pentoxide and 44 g. of kieselguhr is added in incremental portions, and the mixture is stirred for 2.5 hours under nitrogen at room temperature. The solution is filtered and combined with 5.8 ml. of triethylamine. The solvents are distilled off, and the residue is recrystallized from methanol with the addition of activated carbon and 1% triethylamine, thus obtaining 15.6 g. of 21-acetoxy-6-chloro-17α-methoxymethoxy-4,6-pregnadiene-3,20-dione, m.p. 183°–186° C.

EXAMPLE 21

38.85 g. of 21-acetoxy-17α-hydroxy-4-pregnene, 3,20-dione is stirred together with 235 ml. of formaldehyde diisopropylacetal and 500 ml. of methylene chloride and cooled to −20° C. Under agitation, a mixture of 75 g. of phosphorus pentoxide and 150 g. of kieselguhr is introduced and the mixture is agitated for 20 hours at −20° C. The mixture is filtered, washed with methylene chloride, and brought to pH 9 with triethylamine. The solvents are distilled off under vacuum and the residue taken up in methylene chloride. The solution is washed with semisaturated sodium chloride solution, dried with sodium sulfate, treated with activated carbon, vacuum-filtered over kieselguhr, and concentrated under vacuum. The residue is chromatographed on silica gel with toluene/ethyl acetate mixtures.

Yield: 35.8 g. of 21-acetoxy-17α-isopropoxymethoxy-4-pregnene-3,20-dione, m.p. after crystallization with pentane: 111°–117° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A steroid of the formula

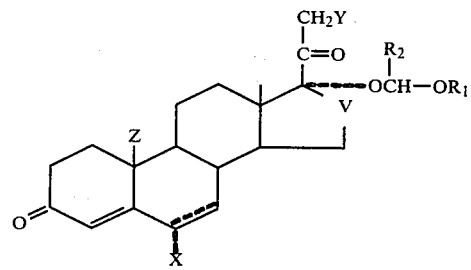

wherein
- $\equiv$ represents a single or double bond,
- X is hydrogen, fluorine or methyl;
- Y is hydrogen, hydroxy or alkanoyloxy of 1–6 carbon atom;
- Z is hydrogen or methyl;
- V is methylene, ethylidene, hydroxymethylene or vinylidene; and
- $R_1$ is alkyl of 1–6 carbon atoms or alkyl of 2–6 carbon atoms with an oxygen atom between two of the carbon atoms,
- $R_2$ is hydrogen or alkyl of 1–6 carbon atoms, or
- $R_1$ and $R_2$ together form a trimethylene group provided that Y is hydroxy or alkanoyloxy.

2. 21-Hydroxy-17 α-methoxymethoxy-4-pregnene-3,20-dione, a compound of claim 1.

3. 21-Acetoxy-17 α-(1'-methoxyethoxy)-4-pregnene-3,20-dione, a compound of claim 1.

4. 21-Acetoxy-17 α-(1'-isobutoxyethoxy)-4-pregnene-3,20-dione, a compound of claim 1.

5. 21-Acetoxy-17 α-(1'-ethoxyethoxy)-4-pregnene-3,20-dione, a compound of claim 1.

6. 21-Acetoxy-17 α-(1'methoxyethoxy)-6 α-methyl-4-pregnene-3,20-dione, a compound of claim 1.

7. 21-Acetoxy-17 α-(1'-methoxyethoxy)-16 β-methyl-4-pregnene-3,20-dione, a compound of claim 1.

8. 17 α-(1'-Methoxyethoxy)-4-pregnene-3,20-dione, a compound of claim 1.

9. 21-Hydroxy-17 α-(2'-methoxyethoxymethoxy)-4-pregnene-3,20-dione, a compound of claim 1.

10. 17 α-Methoxymethoxy-4-pregnene-3,20-dione, a compound of claim 1.

11. 17 α-Methoxymethoxy-19-nor-4-pregnene-3,20-dione, a compound of claim 1.

12. 17 α-Ethoxymethoxy-19-nor-4-pregnene-3,20-dione, a compound of claim 1.

13. 17 α-Propoxymethoxy-19-nor-4-pregnene-3,20-dione, a compound of claim 1.

14. A pharmaceutical composition comprising an anti-inflammatory amount of a compound of claim 1 and a pharmaceutically acceptable carrier.

15. A method of treating inflammation in mammals which comprises administering to the mammal an anti-inflammatory amount of a compound of claim 1.

16. A process for preparing a steroid of claim 1 which comprises reacting a steroid of the formula

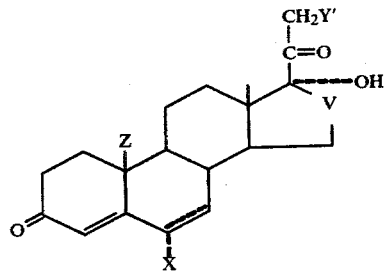

or of the formula

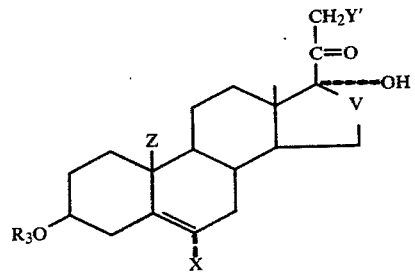

wherein
═, X, V and Z are as defined in claim 1,
Y' is hydrogen or alkanoyloxy of 1–6 carbon atoms, and
R₃ is alkanoyl of 1–6 carbon atoms,
with an acetal of the formula

wherein $R_1$ and $R_2$ are as defined in claim 1 and
optionally saponifying an ester group which is present
or oxidizing a 3 β-hydroxy group with simultaneous isomerization of the Δ⁵-double bond.

17. A method of preparing a steroid of the formula:

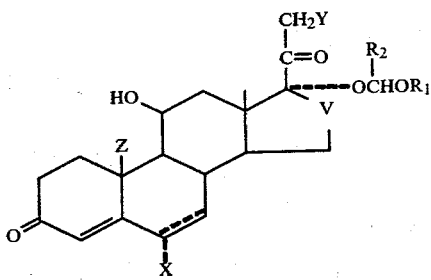

wherein, ═, X, Z, V, Y, $R_1$ and $R_2$ are as defined in claim 1, which comprises, hydroxylating in the 11 α-position a steroid of claim 1.

18. A method of preparing a steroid of the formula:

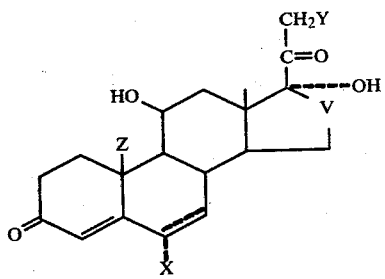

wherein
═, X, Y, Z, V, $R_1$ and $R_2$ are defined in claim 1, which comprises splitting the 17-acetal group of a compound of the formula

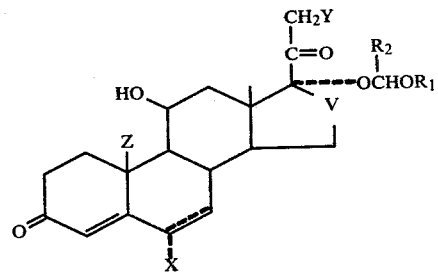

by treating it under acidic conditions effective to cleave the acetal group.

19. 21-Acetoxy-17α-ethoxymethoxy-4-pregnene-3,20-dione, a compound of claim 1.

20. 21-Acetoxy-17α-propoxymethoxy-4-pregnene-3,20-dione, a compound of claim 1.

21. 21-Acetoxy-17α-butoxymethoxy-4-pregnene-3,20-dione, a compound of claim 1.

22. 21-Acetoxy-6α-fluoro-17α-methoxymethoxy-4-pregnene-3,20-dione, a compound of claim 1.

23. 21-Hydroxy-17α-methoxymethoxy-16β-methyl-4-pregnene-3,20-dione, a compound of claim 1.

24. 21-Acetoxy-6-chloro-17α-methoxymethoxy-4,6-pregnadiene-3,20-dione, a compound of claim 1.

25. 21-Acetoxy-17α-isopropoxymethoxy-4-pregnene-3,20-dione, a compound of claim 1.

26. The steroid of claim 1 wherein

R$_1$ is alkyl of 1–6 carbon atoms or alkyl of 2–6 carbon atoms with an oxygen atom between two of the carbon atoms, and R$_2$ is hydrogen or alkyl of 1–6 carbon atoms.

27. A process for preparing a steroid of claim 1 which comprises reacting a steroid of the formula

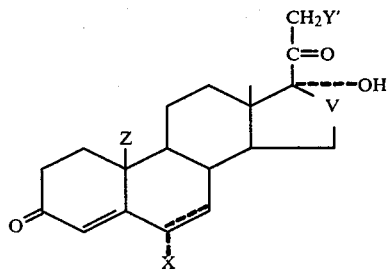

or of the formula

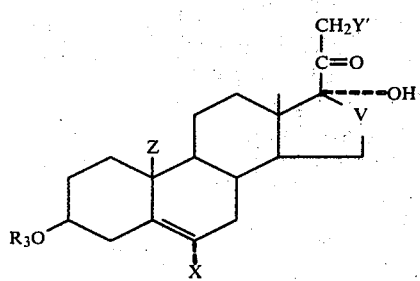

wherein $\equiv$, X, V and Z are as defined in claim 1,

Y' is hydrogen or alkanoyloxy of 1–6 carbon atoms, and

R$_3$ is alkanoyl of 1–6 carbon atoms, with a vinyl ether of the formula

R$_4$CH=CHOR$_1$ wherein

R$_1$ is as defined in claim 1 and

R$_4$ is hydrogen or alkyl of 1–5 carbon atoms, or R$_4$ together with R$_1$ is ethylene when Y, in the steroid of claim 1 to be prepared, is hydroxy or alkanoyloxy; and further, optionally saponifying an ester group which is present or oxidizing a 3 $\beta$-hydroxy group with simultaneous isomerization of the $\Delta^5$-double bond.

* * * * *

UNITED STATES PATENT AND TRADEMARK OFFICE
CERTIFICATE OF CORRECTION

PATENT NO. : 4,224,320
DATED : September 23, 1980
INVENTOR(S) : HELMUT DAHL ET AL It is certified that error appears in the above-identified patent and that said Letters Patent are hereby corrected as shown below:

Column 14, line 21: reads " claim 1, which comprises, hydroxylating in the 11 alpha- "

should reads -- claim 1, which comprises, hydroxylating in the 11 beta- --.

Signed and Sealed this

Twentieth Day of January 1981

[SEAL]

Attest:

RENE D. TEGTMEYER

Attesting Officer

Acting Commissioner of Patents and Trademarks